United States Patent [19]

Bradshaw et al.

[11] 4,144,392

[45] Mar. 13, 1979

[54] CEPHALOSPORINS HAVING AT POSITION-7 A CARBOXY SUBSTITUTED α-ETHERIFIED HYDROXYIMINO-ARYLACETAMIDO GROUP AND AT POSITION-3 THE RESIDUE OF A SULPHUR NUCLEOPHILE

[75] Inventors: Janice Bradshaw, Harrow; Martin C. Cook, Liverpool; Gordon I. Gregory, Chalfont St. Peter, all of England

[73] Assignee: Glaxo Laboratories Limited, Greenford, England

[21] Appl. No.: 696,438

[22] Filed: Jun. 15, 1976

Related U.S. Application Data

[63] Continuation-in-part of Ser. No. 668,529, Mar. 19, 1976, Pat. No. 4,103,084, which is a continuation of Ser. No. 533,451, Dec. 16, 1974, abandoned.

[30] Foreign Application Priority Data

Dec. 21, 1973 [GB] United Kingdom ............... 59517/73

[51] Int. Cl.$^2$ .................. C07D 501/56; A61K 31/545
[52] U.S. Cl. ........................................ 544/27; 544/26; 544/29; 424/246
[58] Field of Search ............... 260/243 C; 544/26, 27, 544/22, 29

[56] References Cited

FOREIGN PATENT DOCUMENTS

| | | |
|---|---|---|
| 806450 | 4/1974 | Belgium. |
| 2204060 | 8/1972 | Fed. Rep. of Germany. |
| 2223375 | 11/1972 | Fed. Rep. of Germany. |
| 2262500 | 7/1973 | Fed. Rep. of Germany. |
| 2460537 | 7/1975 | Fed. Rep. of Germany. |
| 68680 | 1/1974 | Luxembourg. |

*Primary Examiner*—Donald G. Daus
*Assistant Examiner*—D. G. Rivers
*Attorney, Agent, or Firm*—Bacon & Thomas

[57] ABSTRACT

Cephalosporin antibiotics having the formula:

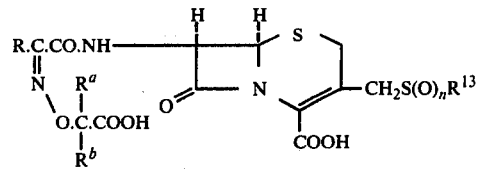

(where R is thienyl, furyl or phenyl; $R^a$ is hydrogen, $C_{1-4}$ alkyl, $C_{2-4}$ alkenyl, $C_{3-7}$ cycloalkyl or phenyl, and $R^b$ is hydrogen, $C_{1-4}$ alkyl, $C_{2-4}$ alkenyl, $C_{3-7}$ cycloalkyl, phenyl, carboxy or $C_{2-5}$ alkoxycarbonyl, or $R^a$ and $R^b$ together with the carbon atom to which they are attached form a $C_{3-7}$ cycloalkylidene or cycloalkenylidene group; $R^{13}$ is $C_1$-$C_6$ alkyl, $C_{3-7}$ cycloalkyl, phenylalkyl, phenyl or naphthyl, thiadiazolyl, diazolyl, triazolyl, tetrazolyl, thiazolyl, thiatriazolyl, oxazolyl, oxadiazolyl, pyridyl, pyrimidyl, benzimidazolyl, benzoxazolyl, benzothiazolyl, triazolopyridyl or purinyl, and n is 0, 1 or 2 and their physiologically acceptable derivatives exhibit broad spectrum antibiotic activity characterized by particularly high activity against gram negative microorganisms, including those which produce β-lactamases. The compounds, which are syn isomers or exist as mixtures of syn and anti isomers containing at least 90% of the syn isomer, have particularly high in vitro activity against strains of *Escherichia coli*, *Haemophilus influenzae* and *Proteus* organisms; and unusually high activity against *Pseudomonas* organisms.

8 Claims, No Drawings

CEPHALOSPORINS HAVING AT POSITION-7 A CARBOXY SUBSTITUTED α-ETHERIFIED HYDROXYIMINO-ARYLACETAMIDO GROUP AND AT POSITION-3 THE RESIDUE OF A SULPHUR NUCLEOPHILE

CROSS REFERENCE TO RELATED APPLICATIONS

This application is a continuation-in-part of our U.S. Application Ser. No. 668,529 filed Mar. 19, 1976, now U.S. Pat. No. 4,103,084, which is a continuation of our U.S. Application Ser. No. 533,451 filed Dec. 16, 1974, now abandoned.

This invention is concerned with improvements in or relating to cephalosporin compounds, and is more particularly concerned with a novel class of cephalosporin compounds possessing valuable antibiotic properties.

The cephalosporin compounds in this specification are named with reference to "cepham" after *J. Amer. Chem. Soc.*, 1962, 84, 3400, the term "cephem" referring to the basic cepham structure with one double bond.

Cephalosporin antibiotics are widely used in the treatment of diseases caused by pathogenic bacteria in human beings and animals, for example in the treatment of diseases caused by bacteria which are resistant to other antibiotics such as penicillin compounds, and in the treatment of penicillin-sensitive patients. In many instances it is desirable to employ a cephalosporin antibiotic which exhibits activity against both gram positive and gram negative microorganisms, and a significant amount of research has been directed to the development of various types of broad spectrum cephalosporin antibiotics.

Considerable interest is currently being directed to the development of broad spectrum cephalosporin antibiotics which possess high activity against gram negative organisms. Existing commercially available β-lactam antibiotics tend to exhibit comparatively low activity against certain gram negative organisms such as Proteus organisms, which are an increasingly common source of infection in humans, and are also generally substantially inactive against Pseudomonas organisms. Several Pseudomonas organisms are resistant to the majority of existing commerically available antibiotic compounds, and the practical therapeutic applications of aminoglycoside antibiotics such as gentamicin which do exhibit Pseudomonas activity tend to be limited or complicated by the high toxicity of these antibiotics. It is well known the cephalosporin antibiotics normally exhibit low toxicity in man, so that the development of broad spectrum cephalosporin antibiotics possessing high activity against gram negative organisms such as strains of Proteus and Pseudomonas fulfils a significant need in chemotherapy.

The present invention provides 7β-acylamidoceph-3-em-4-carboxylic acid antibiotics and non-toxic derivatives thereof. These antibiotics have the formula:

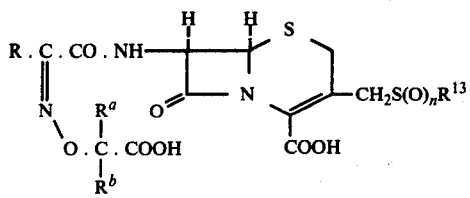

wherein
R is thienyl, furyl or phenyl;
$R^a$ is hydrogen, methyl, ethyl, propyl, isopropyl, butyl, allyl, cyclohexyl or phenyl;
$R^b$ is hydrogen, carboxy, $C_2$-$C_5$ alkoxycarbonyl, methyl, ethyl, propyl, isopropyl, butyl, allyl, cyclohexyl or phenyl; or $R^a$ and $R^b$ together with the carbon atom to which they are attached form a $C_3$-$C_7$ cycloalkylidene, group;
$R^{13}$ is $C_1$-$C_6$ alkyl, $C_3$-$C_7$ cycloalkyl, phenyl $C_1$-$C_6$ alkyl, phenyl, naphthyl, thiadiazolyl, diazolyl, triazolyl, tetrazolyl, thiazolyl, thiatriazolyl, oxazolyl, oxadiazolyl, pyridyl, pyrimidyl, benzimidazolyl, benzoxazolyl, benzothiazolyl, triazolylopyridyl or purinyl, and n is 0, 1 or 2;
and a physiologicaly acceptable salt ester, or 1-oxide thereof.

These compounds exist as syn isomers or exist as mixtures of syn and anti isomers containing at least 90% of the syn isomer.

These compounds exhibit broad spectrum antibiotic activity characterised by particularly high activity against gram negative microorganisms, including those which produce β-lactamases, and also possess very high stability to β-lactamases produced by a range of gram negative organisms. A characteristic feature of the compounds is their high in vitro activity against gram-negative organisms such as *Enterobacter clocae, Serratia marcescens* and *Klebsiella aerogenes*. The compounds have particularly high activity against strains of *Escherichia coli, Haemophilus influenzae* and Proteus organisms, e.g. strains of *Proteus morganii* and *Proteus mirabilis*. Compounds wherein at least one of $R^a$ and $R^b$ is other than hydrogen have also shown unusually high activity against Pesudomonas organisms, for example strains of *Pseudomonas aeruginosa*.

The compounds of the invention are defined as having the syn isomeric form as regards the configuration of the group

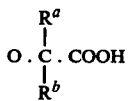

with respect to the carboxamido group. In this specification the syn configuration is denoted structurally as

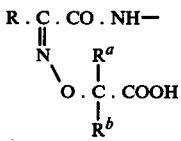

this configuration being assigned on the basis of the work of Ahmad and Spenser reported in *Can. J. Chem.*, 1961, 39, 1340. As indicated above, the compounds may exist as mixtures of syn and anti isomers provided that such mixtures contain at least 90% of the syn isomer. We prefer, however, the compounds to be syn isomers essentially free from the corresponding anti isomer.

By "non-toxic derivatives" is meant those derivatives which are physiologically acceptable in the dosage at which they are administered. Such derivatives may include, for example, salts, biologically acceptable esters, 1-oxides and solvates (especially hydrates). It will be appreciated that derivatives such as salts and esters may be formed by reaction or both of the carboxyl groups present in the compounds of formula I.

Non-toxic salt derivatives which may be formed from the compounds of general formula I include inorganic base salts such as alkali metal salts (e.g. sodium and potassium salts) and alkaline earth metal salts (e.g. calcium salts); organic base salts (e.g. procaine, phenylethylbenzylamine, dibenzylethylenediamine, ethanolamine, diethanolamine, triethanolamine and N-methylglucosamine salts); and, where appropriate, acid addition salts, e.g. with hydrochloric, hydrobromic, sulphuric, nitric, phosphoric, trifluoroacetic, toluene-p-sulphonic and methane sulphonic acids. The salts may also be in the form of resinates formed with, for example, a polystyrene resin or cross-linked polystyrene divinylbenzene copolymer resin containing amino or quaternary amino groups, or, where appropriate, sulphonic acid groups, or, again where appropriate, with a resin containing carboxyl groups, e.g. a polyacrylic acid resin. Use of highly soluble base salts (e.g. alkali metal salts such as the sodium salt) of compounds of formula I is generally advantageous in the therapeutic applications because of the rapid distribution of such salts in the body upon administration. Where, however, insoluble salts of compounds (I) are desired in a particular application, e.g. for use in depot preparations, such salts may be formed in conventional manner, for example with appropriate organic amines.

Biologically acceptable, metabolically labile ester derivatives which may be formed from compounds of formula I include, for example, acyloxymethyl esters, e.g. lower alkanoyloxymethyl esters such as acetoxymethyl or pivaloyloxymethyl esters.

Where the group R in the above formulae is a furyl group it may be fur-2-yl or fur-3-yl and where it is a thienyl group it may be thien-2-yl or thien-3-yl.

It will be appreciated that when $R^a$ and $R^b$ in the above formulae are different, the carbon atom to which they are attached may comprise a centre of asymmetry; compounds in accordance with the invention wherein $R^a$ and $R^b$ are different may thus be diastereoisomeric. The invention embraces the individual diastereoisomers of such compounds as well as mixtures thereof.

The term "lower" as used in this specification and the accompanying claims to qualify aliphatic groups denotes, unless otherwise stated, that the said group may contain up to 6 carbon atoms. "Lower" as used to qualify cycloaliphatic groups indicated that the group may contain 3–7 (e.g. 5–7) carbon atoms.

A particularly interesting class of cephalosporin antibiotics in accordance with the invention comprises compounds of general formula

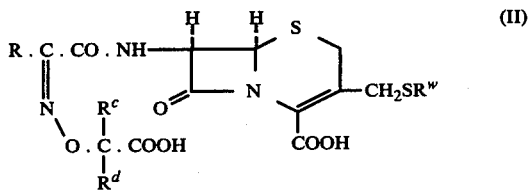

(II)

[wherein R is thienyl or furyl, $R^c$ represents methyl, ethyl, propyl, allyl or phenyl and $R^d$ represents hydrogen, carboxy or, more preferably, a group as defined for $R^c$; or $R^c$ and $R^d$ together with the carbon atom to which they are attached form a cyclobutylidene, cyclopentylidene or cyclohexylidene group; and $R^w$ is selected from pyridyl, diazolyl, triazolyl, tetrazolyl, thiazolyl, thiadiazolyl, oxadiazolyl, and substituted (e.g. lower alkyl- or phenyl-substituted) versions of these groups such as N-methylpyrid-2-yl, 1-methyltetrazol-5-yl, 1-phenyltetrazol-5-yl; 5-methyl-1,3,4-thiadiazol-2-yl and 5-phenyl-1,3,4-oxadiazol-2-yl] and non-toxic derivatives thereof.

These compounds exhibit broad spectrum abtibiotic activity (including very high activity against strains of *Haemophilus influenzae* and Proteus organisms) and high β-lactamase stability and are further characterised by particularly high in vitro activity against Pseudomonas organisms such as strains of *Pseudomonas aeruginosa*.

Especially preferred compounds of the above type, by virtue of their particularly high levels of activity against Proteus and Pseudomonas organisms, include the following:

(6R,7R)-7-[2-(2-carboxyprop-2-yloxyimino)-2-(fur-2-yl)acetamido]-3-(5-methyl-1,3,4-thiadiazol-2-ylthiomethyl)ceph-3-em-4-carboxylic acid (syn isomer), (6R,7R)-7-[2-(1-carboxycyclopent-1-yloxyimino)-2-(fur-2-yl)acetamido]-3-(1-methyltetrazol-5-ylthiomethyl) ceph-3-em-4-carboxylic acid (syn isomer), (6R,7R)-7-[2-(1-carboxycyclobut-1-yloxyimino)-2-(fur-2-yl)acetamido]-3-(1-methyltetrazol-5-ylthiomethyl) ceph-3-em-4-carboxylic acid (syn isomer), (6R,7R)-7-[2-(2-carboxyprop-2-yloxyimino)-2-(fur-2-yl)acetamido]-3-(1-methyltetrazol-5-ylthiomethyl)ceph-3-em-4-carboxylic acid (syn isomer), (6R,7R)-7-[2-carboxymethoxyimino-2-(fur-2-yl)acetamido]-3-(triazol-4-ylthiomethyl)ceph-3-em-4-carboxylic acid (syn isomer), and non-toxic derivatives thereof, e.g. alkali metal salts such as the sodium or potassium salts.

A further interesting class of cephalosporin antibiotics in accordance with the invention comprises compounds of general formula

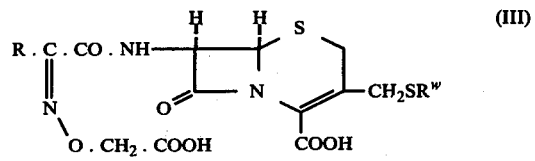

(III)

[wherein R is thienyl or furyl and $R^w$ is as hereinbefore defined] and non-toxic derivatives thereof.

These compounds exhibit broad spectrum antibiotic activity coupled with high β-lactamase stability. A characteristic feature of the compounds is their high activity against strains of *Haemophilus influenzae* coupled with their particularly high activity against strains of *Escherichia coli* and Proteus organisms.

A preferred compound of the above type, by virtue of its particularly high levels of activity against *Escherichia coli* and Proteus organisms, is:

(6R,7R)-7-[2-carboxymethoxyimino-2-(fur-2-yl)acetamido]-3-(1-methyltetrazol-5-ylthiomethyl)ceph-3-em-4-carboxylic acid (syn isomer), and non-toxic derivatives thereof, e.g. alkali metal salts such as the sodium or potassium salts.

The compounds according to the invention may be prepared by any convenient method, for example by techniques analogous to those described in Belgian Pat. No. 783,449.

Thus according to one embodiment of the invention we provide a process for the preparation of an antibiotic compound of general formula I as hereinbefore defined or a non-toxic derivative thereof which comprises either (A) condensing a compound of the formula

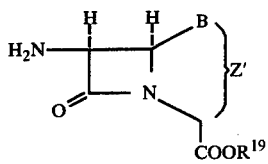

[wherein B is $>$ S or $>$ S $\rightarrow$ O ($\alpha$- or $\beta$-:); $R^{19}$ represents hydrogen or a carboxyl blocking group, e.g. the residue of an ester-forming aliphatic or araliphatic alcohol or an ester-forming phenol, silanol or stannanol (the said alcohol, phenol, silanol or stannanol preferably containing 1-20 carbon atoms) or a symmetrical or mixed anhydride group derived from an appropriate acid; and Z' is a group in which 2 carbon atoms link the nuclear sulphur atom and the 4-position carbon atom so that the compound possesses $\Delta^2$ or $\Delta^3$ unsaturation] or a salt, e.g. an acid addition salt such as a hydrochloride, hydrobromide, sulphate, nitrate, phosphate, methane sulphonate or tosylate, or an N-silylated derivative thereof with an acylating agent corresponding to an acid of formula

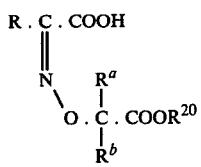

(wherein R, $R^a$, $R^b$, m and n are as hereinbefore defined and $R^{20}$ is a carboxyl blocking group, e.g. a group as hereinbefore defined in connection with $R^{19}$); or (B), reacting a compound of the formula

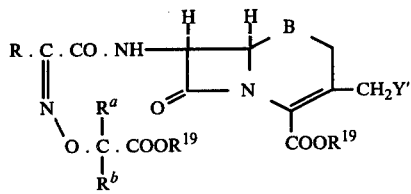

(wherein B, R, $R^a$, $R^b$, m and n are as hereinbefore defined; each $R^{19}$ may independently represent hydrogen or a carboxyl blocking group; Y' is a replaceable residue of a nucleophile, e.g. an acetoxy or dichloroacetoxy group or a halogen atom such as chlorine, bromine or iodine; and the dotted line bridging the 2-, 3- and 4-positions indicates that the compound is a ceph-2-em or ceph-3-em compound) with an appropriate sulphur nucleophile; whereafter, if necessary and/or desired in each instance, any of the following reactions (C) in any appropriate sequence, are carried out:

(i) conversion of a $\Delta^2$ isomer into the desired $\Delta^3$ isomer,
(ii) reduction of a compound wherein B is $>$S$\rightarrow$O to form a compound wherein B is $>$S,
(iii) removal of carboxyl blocking groups; and finally (D) recovering the desired compound of formula I or a non-toxic derivative thereof, if necessary after separation of isomers.

Non-toxic derivatives of the compounds of formula I may be formed in any convenient way, for example according to methods well known in the art. Thus, for example, base salts may be formed by reaction of the cephalosporin acid with sodium 2-ethylhexanoate or potassium 2-ethylhexanoate. Biologically acceptable ester derivatives may be formed using conventional esterifying agents. 1-Oxides may be formed by treatment of the corresponding cephalosporin sulphide with an appropriate oxidising agent, for example with a peracid such as metaperiodic acid, peracetic acid, monoperphthalic acid or m-chloroperbenzoic acid, or with t-butyl hypochlorite, this last reagent conveniently being employed in the presence of a weak base such as pyridine.

Acylating agents which may be employed in the preparation of compounds of formula I include acid halides, particularly acid chlorides or bromides. Such acylating agents may be prepared by reacting an acid (V) or a salt thereof with a halogenating agent e.g. phosphorus pentachloride, thionyl chloride or oxalyl chloride. Treatment of the sodium, potassium or triethylammonium salt of the acid (V) with oxalyl chloride is advantageous in that under these conditions isomerisation is minimal.

Acylations employing acid halides may be effected in aqueous and non-aqueous reaction media, conveniently at temperatures of from $-50°$ to $+50°$ C., preferably $-20°$ to $+30°$ C., if desired in the presence of an acid binding agent. Suitable reaction media include aqueous ketones such as aqueous acetone, esters such as ethyl acetate, halogenated hydrocarbons such as methylene chloride, amides such as dimethylacetamide, nitriles such as acetonitrile, or mixtures of two or more such solvents. Suitable acid binding agents include tertiary amines (e.g. triethylamine or dimethylaniline), inorganic bases (e.g. calcium carbonate or sodium bicarbonate), and oxiranes such as lower 1,2-alkylene oxides (e.g. ethylene oxide or propylene oxide) which bind hydrogen halide liberated in the acylation reaction.

Acids of formula V may themselves be used as acylating agents in the preparation of compounds of formula I. Acylations employing acids (V) are desirably conducted in the presence of a condensation agent, for example a carbodiimide such as N,N'-diethyl-, dipropyl- or diisopropylcarbodiimide, N,N'-dicyclohexylcarbodiimide or N-ethyl-N'-$\gamma$-dimethylaminopropylcarbodiimide; a carbonyl compound such as carbonyldiimidazole; or an isoxazolinium salt such as N-ethyl-5-phenylisoxazolinium perchlorate. Acylation reactions of this type are desirably effected in an anhydrous reaction medium, e.g. methylene chloride, dimethylformamide or acetonitrile.

Acylation may also be effected with other amide-forming forming derivatives of acids of formula V such as, for example, a symmetrical anhydride or a mixed anhydride (e.g. with pivalic acid or formed with a haloformate such as a lower alkylhaloformate). The mixed or symmetrical anhydride may be generated in situ; thus, for example, a mixed anhydride may be generated using N-ethoxycarbonyl-2-ethoxy-1,2-dihydroquinoline. Mixed anhydrides may also be formed with phosphorus acids (for example phosphoric or phosphorous acids), sulphuric acid or aliphatic or aromatic sulphonic acids (for example p-toluene sulphonic acid).

It will be appreciated that in processes for the preparation of compounds of formula I wherein $R^a$ or $R^b$ represents carboxy it will in many instances be necessary to protect the carboxy group, for example by substitution with a carboxyl blocking group, e.g. a group as hereinbefore defined in connection with $R^{19}$.

Any transformations of substituents at the 3-position which may be necessary in the preparation of particular compounds of formula I may, for example, be effected by methods described in the literature.

Compounds of formula I may be prepared by the reaction of a 3-acetoxymethyl cephalosporin compound with an appropriate sulphur-linking, nucleophile as described in British Pat. Nos. 1,012,943, 1,059,562, 1,101,423 and 1,206,305.

Compounds of formula I may also be prepared by the reaction of a 3-halomethylcephalosporin with an appropriate sulphur nucleophile disclosed in the above references, such a process being described in British Pat. No. 1,241,657, or by the reaction of a 3-halomethylcephalosporin sulphoxide with any appropriate sulphur nucleophile disclosed in the above references, such a process being described in British Pat. No. 1,326,531. The contents of the above mentioned British Patents are herein incorporated for reference purposes.

Appropriate sulphur nucleophiles are those compounds of the formula: $R^{13a} \cdot S(O)_n H$ in which $R^{13a}$ is an aliphatic e.g. lower alkyl such as methyl, ethyl or n-propyl group; an alicyclic e.g. lower cycloalkyl such as cyclohexyl or cyclopentyl group; an aromatic e.g. $C_{6-12}$ mono- or bicyclic carbocyclic aryl such as phenyl or naphthyl group; an araliphatic e.g. phenyl lower (e.g. $C_{1-4}$) alkyl such as benzyl group; or a heterocyclic group, and n is 0, 1 or 2. A preferred class of nucleophiles falling within the above formula is that having the general formula $R^{14}$ SH in which $R^{14}$ is aliphatic, e.g. lower alkyl such as methyl, ethyl or n-propyl or lower alkanoyl such as acetyl; araliphatic, e.g. phenyl lower alkyl such as benzyl or phenethyl or substituted phenyl lower alkyl; alicyclic, e.g. cycloalkyl such as cyclopentyl or cyclohexyl; aromatic, e.g. phenyl, substituted phenyl or a heterocyclic group containing at least one 5- or 6-membered ring and having one or more heteroatoms selected from O, N and S. Such heterocyclic groups $R^{14}$ may be substituted, and examples of suitable heterocylic groups includes thiadiazolyl, e.g. 5-methyl-1,3,4-thiadiazol-2-yl; diazolyl; triazolyl, e.g. triazol-4-yl; tetrazolyl, e.g. 1-methyltetrazol-5-yl, 1-ethyltetrazol-5-yl or 1-phenyltetrazol-5-yl; thiazolyl; thiatriazolyl; oxazolyl; oxadiazolyl, e.g. 2-phenyl-1,3,4-oxadiazol-5-yl; pyridyl, e.g. N-methylpyrid-2-yl; pyrimidyl; fused heterocyclic ring systems such as benzimidazolyl, benzoxazolyl, benzothiazolyl such as benzothiazol-2-yl, triazolopyridyl or purinyl; and substituted versions of such fused ring systems, e.g. nitrobenzothiazol-2-yl such as 5- or 6-nitrobenzothiazol-2-yl.

$\Delta^2$-Cephalosporin ester derivatives obtained in accordance with the process of the invention may be converted into the corresponding $\Delta^3$ derivative by, for example, treatment of the $\Delta^2$ ester with a base.

Ceph-2-em reaction products may also be oxidised to yield the corresponding ceph-3-em 1-oxide, for example by reaction with a peracid as mentioned previously; the resulting sulphoxide may, if desired, subsequently be reduced as described hereinafter to yield the corresponding ceph-3-em sulphide.

Where a compound is obtained in which B is >S→O this may be converted to the corresponding sulphide by, for example, reduction of the corresponding acyloxysulphonium or alkyloxysulphonium salt prepared in situ by reaction with e.g. acetyl chloride in the case of an acetoxysulphonium salt, reduction being effected by, for example, sodium dithionite or by iodide ion as in a solution of potassium iodide in a water miscible solvent e.g. acetic acid, tetrahydrofuran, dioxan, dimethylformamide or dimethylacetamide. The reaction may be effected at a temperature of $-20°$ to $+50°$ C.

Where a compound of formula I is obtained as a mixture of isomers, the syn isomer may be obtained by, for example, conventional methods such as crystallisation or chromatography. Syn and anti isomers may be distinguished by appropriate techniques, e.g. by their ultraviolet spectra, by thin layer or paper chromatography or by their proton magnetic resonance spectra. Thus, for example, the p.m.r. spectra of DMSO-$d_6$ solutions of syn compounds of Formula I exhibit the doublet for the amide NH at a lower field than do similar solutions of the corresponding anti-isomers. These factors may be employed in monitoring reactions.

Acids (V) may be obtained by reacting a glyoxylic acid of formula

R·CO·COOH                     (VII)

(where R has the above-defined meaning) or an ester thereof with a hydroxylamine derivative of formula

(where $R^a$, $R^b$, and $R^{20}$, have the above-defined meanings). The resulting acid or ester may be separated into its syn and anti isomers by, for example, crystallisation, chromatography or distillation, whereafter ester derivatives may be hydrolysed to yield the corresponding acid.

Acids (V) may also be prepared by etherification of an acid of formula

(where R has the above-defined meaning), e.g. by reaction with a compound of general formula

(wherein $R^a$, $R^b$, and $R^{20}$, are as hereinbefore defined and T is halogen such as chloro, bromo or iodo; sulphate; or sulphonate such as tosylate). Separation of isomers may be effected either before or after such etherification. The etherification reaction is desirably carried out in the presence of a base, e.g. potassium t-butoxide or sodium hydride, and is preferably conducted in an organic solvent, for example dimethylsulphoxide, a cyclic ether such as tetrahydrofuran or dioxan, or an N,N-disubstituted amide such as dimethylformamide. Under these conditions the configuration of the oximino group is substantially unchanged by the etherification reaction.

Acids of formula V and acylating agents derived therefrom (e.g. acyl halides such as the chloride) are novel and comprise a feature of the present invention.

Derivatives of the compounds of the invention in which the carboxy substituent of the 7β-acylamido side chain is substituted by a carboxyl blocking group are also new and comprise a feature of the invention. These monoester derivatives, which may be represented by the general formula

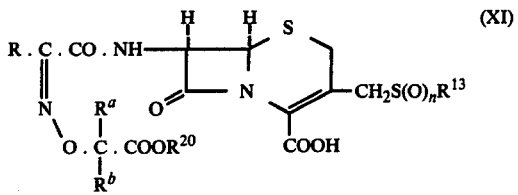

(XI)

(wherein R, $R^1$, $R^b$, $R^{13}$ and n are as hereinbefore defined and $R^{20}$ is a carboxyl blocking group such as t-butyl or diphenylmethyl), are of value as intermediates in the preparation of antibiotic compounds of general formula I. The compounds may themselves exhibit antibiotic activity, although generally at a very low level when compared to corresponding compounds (I).

Carboxyl blocking groups $R^{20}$ and, where appropriate, $R^{19}$ used in the preparation of compounds of formula I or in the preparation of necessary starting materials are desirably groups which may readily be split off at a suitable stage in the reaction sequence, conveniently as the last stage. It may, however, be convenient in some instances to employ biologically acceptable, metabolically labile carboxyl blocking groups such as acyloxymethyl groups (e.g. pivaloyloxymethyl) and retain these in the final product to give a biologically acceptable ester derivative of a compound of formula I.

Suitable carboxyl blocking groups are well known in the art, a list of representative blocked carboxyl groups being included in Belgian Pat. No. 783,449. Preferred blocked carboxyl groups include aryl lower alkoxycarbonyl groups such as p-methoxybenzyloxycarbonyl, p-nitrobenzyloxycarbonyl and diphenylmethoxycarbonyl; lower alkoxycarbonyl groups such as t-butoxycarbonyl; and lower haloalkoxycarbonyl groups such as 2,2,2-trichloroethoxycarbonyl. The carboxyl blocking group may subsequently be removed by any of the appropriate methods disclosed in the literature; thus, for example, acid or base catalysed hydrolysis is applicable in many cases, as are enzymically-catalysed hydrolyses.

The antibiotic compounds of the invention, e.g. compounds of formula I and non-toxic derivatives thereof, may be formulated for administration in any convenient way, by analogy with other antibiotics and the invention therefore includes within its scope pharmaceutical compositions comprising an antibiotic compound in accordance with the invention adapted for use in human or veterinary medicine. Such compositions may be presented for use in conventional manner with the aid of any necessary pharmaceutical carriers or excipients.

The antibiotic compounds according to the invention may be formulated for injection and may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for reconstitution with a suitable vehicle, e.g. sterile, pyrogen-free water, before use.

The antibiotic compounds may also be presented in a form suitable for absorption by the gastro-intestinal tract. Tablets and capsules for oral administration may be in unit dose presentation form, and may contain conventional excipients such as binding agents, for example syrup, acacia, gelatin, sorbitol, tragacanth or polyvinylpyrollidone; fillers, for example lactose, sugar, maize-starch, calcium phosphate, sorbitol or glycine; lubricants, for example magnesium stearate, talc, polyethylene glycol or silica; disintegrants, for example potato starch; or acceptable wetting agents such as sodium lauryl sulphate. The tablets may be coated according to methods well known in the art. Oral liquid preparation may be in the form of, for example, aqueous or oily suspensions, solutions, emulsions, syrups or elixirs, or may be presented as a dry product for reconstitution with water or other suitable vehicle before use. Such liquid preparation may contain conventional additives such as suspending agents, for example sorbitol syrup, methyl cellulose, glucose/sugar syrup, gelatin, hydroxyethylcellulose, carboxymethyl cellulose, aluminium stearate gel or hydrogenated edible fats; emulsifying agents, for example lecithin, sorbitan mono-oleate or acacia; non-aqueous vehicles (which may include edible oils), for example almond oil, fractionated coconut oil, oily esters, propylene glycol or ethyl alcohol; and preservatives, for example methyl or propyl p-hydroxybenzoates or sorbic acid. The antibiotic compounds may also be formulated as suppositories, e.g. containing conventional suppository bases such as cocoa butter or other glyceride.

Compositions for veterinary medicine may, for example, be formulated as intramammary preparations in either long acting or quick-release bases.

The compositions may contain from 0.1% upwards, e.g. 0.1–99%, preferably from 10–60% of the active material, depending on the method of administration. When the compositions comprise dosage units, each unit will preferably contain 50–1500 mg of the active ingredient. The dosage as employed for adult human treatment will preferably range from 500 to 5000 mg per day, depending on the route and frequency of administration, although in treating Pseudomonas infections higher daily doses may be required.

The antibiotic compounds according to the invention may be administered in combination with other therapeutic agents such as antibiotics, for example penicillins, tetracyclines or other cephalosporins.

The following examples illustrate the invention. All temperatures are in ° C. The structure of the products were verified by p.m.r. spectroscopy (Preparations and Examples) and i.r. spectroscopy (Examples only).

PREPARATION 1

2-t-Butoxycarbonylmethoxyimino-2-(fur-2-yl)acetic acid (syn isomer)

The pH of a mixture of fur-2-ylglyoxylic acid (4.2g), t-butoxycarbonylmethoxyamine (4.5g) and water (50 ml) was adjusted to 5.0 with 2N sodium hydroxide solution. The resulting solution was stirred for 16 hours. The pH of the solution was increased to 7.0, and the solution was washed twice with ether. The aqueous solution was acidified to pH 1.8 under ether, and further extracted with ether. The combined ether extracts were washed (water, saturated brine), dried, and concentrated to give a solid (7.62g), which was crystallised from carbon tetrachloride to give the title compound (3.67g, 46%) m.p. 105.1°–106.2°; $\lambda_{max}$ (pH6 phosphate buffer) 277.5 nm ($\epsilon$ 16,300).

PREPARATION 2

2-(2-t-Butoxycarbonylprop-2-yloxyimino)-2-(fur-2-yl)acetic acid (syn isomer)

A solution of 2-(fur-2-yl)-2-hydroxyiminoacetic acid (syn isomer) (14.1g) in dimethyl sulphoxide (100ml) was added all at once to a magnetically stirred solution of potassium t-butoxide (22.4g) in dimethyl sulphoxide (400ml), the reaction mixture being maintained under an atmosphere of dry nitrogen. A gel was formed which, on stirring, became a finely divided, yellow solid. Stirring was continued for one hour, and then a solution of t-butyl 2-bromo-2-methylpropionate (24.0g) in dimethyl sulphoxide (50ml) was added over one hour to the reaction mixture at room temperature. After addition was complete, the resulting solution was stirred for a further hour. The reaction was poured into ice-water (1.5 liters) and acidified under ether (500ml) to pH 1.8 with concentrated hydrochloric acid. The two layers were separated and the aqueous layer was extracted with more ether. The combined ether extracts were washed once with water, then extracted with aqueous sodium bicarbonate solution. The combined alkaline extracts were acidified under ether to pH 1.8 with concentrated hydrochloric acid, and the acid solution was extracted further with ether. The combined ether extracts were washed (water, saturated brine), dried, and concentrated to a yellow oil, which crystallised under high vacuum (22.41g, 83%), $\lambda_{max}$ (EtOH) 272.5nm ($\epsilon$ 15,400).

The above solid (22.4g) was crystallised from carbon tetrachloride (25ml) to give the title compound (16.42g, 61%), m.p. 72.5°–74.2° (73.0°).

PREPARATIONS 3 AND 4

Method

The dipotassium salt of 2-(fur-2-yl)-2-hydroxyimino acetic acid (syn isomer) was generated under an atmosphere of dry nitrogen and alkylated with the appropriate halo-t-butyl ester as described in Preparation 2. The products were isolated by pouring into water, acidifying, and extracting in the conventional manner.

EXAMPLE 1

(6R,7R)-7-[2-Carboxymethoxyimino-2-(fur-2-yl)-acetamido]-3-(1-methyltetrazol-5-ylthiomethyl)ceph-3-em-4-carboxylic acid (syn isomer)

A solution of 2-t-butoxycarbonylmethoxyimino-2-(fur-2-yl)acetic acid (syn isomer) (0.97g) in methylene chloride (20ml) was added dropwise at room temperature over 15 minutes to a stirred solution of diphenylmethyl (6R,7R)-7-amino-3-(1-methyltetrazol-5-ylthiomethyl)ceph-3-em-4-carboxylate (1.484 g) and dicyclohexylcarbodiimide (0.743g) in methylene chloride (45 ml). After stirring for a further 2 hours the solvent was removed by evaporation, and the residue was stirred for 5 minutes with ethyl acetate (50 ml) and filtered. The filtrate was washed with saturated sodium bicarbonate solution, diluted with an equal volume of water and then with brine (25 ml of each), dried and evaporated to a foam (2.5 g) which was dissolved in benzene and purified by chromatography on Kieselgel (70 g). Elution with benzene:ethyl acetate (10:1), combination of appropriate fractions and evaporation to dryness gave a foam (2.05g) which was dissolved in ethyl acetate and run into light petroleum to give diphenylmethyl (6R,7R)-7-[2-t-butoxycarbonylmethoxyimino-2-(fur-2-yl)-acetamido]-3-(1-methyltetrazol-5-ylthiomethyl)ceph-3-em-4-carboxylate (syn isomer) (2.02 g, 90%) as a white amorphous solid, $[\alpha]_D^{23}$ $-102°$ (c 0.99,CHCl$_3$); $\lambda_{max}$ (EtOH) 278 nm ($\epsilon$ 19,800).

A solution of this diester (1.93 g) in a mixture of trifluoroacetic acid (7.7 ml) and anisole (1.9 ml) was kept at 0° for 10 minutes and then added to a mixture of saturated sodium bicarbonate and water (1:3, 850 ml). After stirring for 10 minutes the mixture was washed with ethyl acetate, covered with more ethyl acetate (200 ml) and acidified to pH 2 with concentrated hydrochloric acid. The organic phase was separated, washed with water and brine, dried and evaporated to a foam (1.54 g). Thin layer chromatography suggested that deprotection was incomplete and the product was retreated with trifluoroacetic acid (4.3 ml) and anisole (1.1 ml) at 20° for 15 minutes, whereafter the product was isolated as a foam (1.3 g) as described above. This foam in ethyl acetate was run into light petroleum to give the title dicarboxylic acid (0.8 g, 59%) as a white amorphous solid, $[\alpha]_D^{23}$ $-99°$ (c 105, acetone); $\lambda_{max}$ (0.1M-pH 6 phosphate buffer) 277nm ($\epsilon$ 21,900); $\nu_{max}$ (Nujol) 1780 cm$^{-1}$; $\tau$(d$_6$-DMSO) values include 0.19(d$_1$ NH), 4.14(dd, 7-H), 5.30 (S·CH$_2$CO$_2$H).

TABLE 1

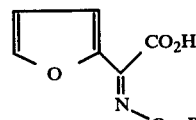

| Preparation No. | R$^q$ | R$^{20}$ | Method | m.p. °C | $\lambda_{max}$,nm (solvent) | $\epsilon$ | $\tau$ values for d$_6$-DMSO R$^q$ | R$^{20}$ |
|---|---|---|---|---|---|---|---|---|
| 3 | ⌖ | —C(CH$_3$)$_3$ | A | 106.8–107.3° | 277.5(pH6 buffer) | 15,100 | 8.03; 8.30 | 8.63 |
| 4 | ⌖ | —C(CH$_3$)$_3$ | A | 113–114° | 278 (pH6 buffer) | 17,200 | 7.4–8.3 | 8.59 |

EXAMPLES 2-5

General Procedure for the Preparation of (6R,7R)-7-[2-carboxy-$R^q$-oxyimino-2-(fur-2-yl)acetamido]-3-(substituted)-ceph-3-em-4-carboxylic acids (syn isomers) using Dicyclohexylcarbodiimide (i) To a solution of a diphenylmethyl (6R,7R)-7-amino-3-(substituted)ceph-3-em-4-carboxylate (1 equiv) and dicyclohexylcarbodiimide (1–1.3 equiv) in dry methylene chloride was added at 0°–25° a solution of the appropriate 2-t-butoxycarbonyl-$R^q$-oxyimino-2-(fur-2-yl)acetic acid (syn isomer) (1–1.15 equiv) in dry methylene chloride. After stirring for 0.5–5.0 hours the dicyclohexylurea was removed by filtration and the filtrate was evaporated. The residue in ethyl acetate or methylene chloride was washed successively with aqueous sodium bicarbonate, water and brine, dried and evaporated. The diester was purified by chromatography on silica or, after decolourisation with charcoal, by trituration or crystallisation. The product was characterised by its p.m.r. spectrum and by thin layer chromatography.

Where the 7-amino starting material was available as an acid addition salt the free base was liberated by shaking with a mixture of ethyl acetate (or methylene chloride) and an excess of an aqueous solution of sodium bicarbonate. After washing with water and brine the organic layer was evaporated to dryness and the free amine used as described above.

(ii) Method A: The intermediate diesters so derived were deprotected by dissolving in a mixture of trifluoracetic acid (3–10 ml/1 g of diester) and anisole (0.8–12 ml/1 g of diester) and left at between 0° and room temperature for between 5 minutes and 2.5 hours. The mixture was concentrated under reduced pressure and added to a mixture of ethyl acetate or ether and excess aqueous sodium bicarbonate, and the aqueous layer was washed with ethyl acetate. The aqueous phase was covered with ethyl acetate and acidified to pH 1–2 with hydrochloric acid. The organic layer was washed, dried and evaporated to give the required dicarboxylic acid.

(ii) Method B: In some cases where treatment with trifluoroacetic acid was insufficient to complete deprotection the intermediate monoester (usually the t-butoxycarbonyl group was cleaved more slowly than the diphenylmethoxycarbonyl group) was retreated with trifluoracetic acid and anisole and the diacid isolated as described above.

The properties of the reaction products are listed in Table 2.

| Ex. No | $R^q$ | P | Method | $[\alpha]_D$ (solvent) | $\lambda_{max}$, nm (solvent) | $\epsilon$ | β-lactam $\nu_{max}$, cm$^{-1}$ (Nujol) | τ values for d$_6$-DMSO at 100 MHz | | |
|---|---|---|---|---|---|---|---|---|---|---|
| | | | | | | | | x | y | $R^q$ |
| 2 | >C(CH$_3$)$_2$ | —CH$_2$S-[N—N / N(CH$_3$)—N] | B | −12° (H$_2$O) | 278 (pH 6 buffer) | 20,050 | 1781 | 0.33 | 4.1 | 8.51 |
| 3 | >C(CH$_3$)$_2$ | —CH$_2$S-[N—N / S—C(CH$_3$)] | A | −48° (DMSO) | 278 (pH 6 buffer) | 21,800 | 1780 | 0.38 | 4.1 | 8.49; 8.57 |
| 4 | (cyclopentyl) | CH$_2$S-[benzoxazole] | A | −89° (DMSO) | 221 283 (pH 6 buffer) | 23,900 21,550 | 1772 | 0.42 | 4.10 | 7.9; 8.3 |
| 5 | (cyclopentyl) | —CH$_2$S-[N—N / N(CH$_3$)—N] | A | −71° (CHCl$_3$) | 279 (pH 6 buffer) | 22,000 | 1780 | 0.42 | 4.15 | 7.9; 8.28 |

EXAMPLES 6-7

General Procedure for the Preparation of (6R,7R)-3-(substituted)-7-[2-(carboxy-$R^q$-oxyimino)-2-(fur-2-yl)acetamido]-ceph-3-em-4-carboxylic Acids (syn-isomers) by Treating an Ester of a (6R,7R)-3-(substituted) 7-aminoceph-3-em-4-carboxylic Acid with an Acid Chloride (syn-isomer)

A solution of the appropriate 2-(t-butoxycarbonyl-$R^q$-oxyimino)-2-(fur-2-yl)acetic acid (syn-isomer) in methylene chloride optionally containing a few drops of N,N-dimethylformamide and triethylamine (1 equiv.) was treated with oxalylchloride (1 equiv.) at 0°–5° for ca 1 hour. A solution of the resulting acid chloride (1–1.3 equiv) in methylene chloride was added dropwise at −5° to +5° over a period of 10–30 minutes to a solution of diphenylmethyl (6R,7R)-3-(substituted)-7-aminoceph-3-em-4-carboxylate (1 equiv) in dry methylene chloride containing propylene oxide (5–20 equiv). The reaction mixture was stirred for ca 1–3 hours at 0° to room temperature and then washed successively with 2N-hydrochloric acid, aqueous sodium bicarbonate, water and/or brine. The dried organic layer was evaporated and the residue purified by trituration, precipitation, chromatography or crystallisation.

The resulting diphenylmethyl (6R,7R)-3-(substituted)-7-[2-(t-butoxycarbonyl-$R^q$-oxyimino)-2-(fur-2-yl)-acetamido]ceph-3-em-4-carboxylate (syn isomer) was deprotected as described for the diesters described in Examples 2–5, Methods A and B. Products are listed in Table 3.

romethane (80 ml) containing propylene oxide (15 ml) at 0°. The mixture was stirred for 1 hour during which time the temperature rose to 20° and the suspension cleared. The resulting yellow solution was washed with 2.5% aqueous sodium bicarbonate solution (50 ml) and then 2N-hydrochloric acid (50 ml), whereafter the solution was dried and evaporated to a yellow oil. This material, in ethyl acetate (20 ml), was added dropwise Table 3

| Ex. No. | $R^q$ | P | Method | $[\alpha]_D$ (solvent) | $\gamma_{max}$,nm (pH6 buffer) | $\epsilon$ | β-lactam $\nu_{max}$,cm$^{-1}$ (Nujol) | τ values for d$_6$-DMSO at 100 MHz | | |
|---|---|---|---|---|---|---|---|---|---|---|
| | | | | | | | | x | y | $R^q$ |
| 6 | —CH$_2$— | CH$_2$S-(imidazole-type ring with N, N, N-H) | A | −38° (DMSO) | 277.5 | 23,600 | 1775 | 0.21 | 4.19 | 5.30 |
| 7 | (cyclobutylidene) | —CH$_2$S-(triazole ring with N-CH$_3$) | A | −97.3° (CHCl$_3$) | 279 | 21,900 | 1782 | 0.32 | 4.11 | 7.6;8.1 |

EXAMPLE 8

The trifluoroacetate salt listed in Table 4 was prepared by reacting the 3-bromomethyl ester (see below) with a quaternary mercaptan, reducing the sulphoxide and removing both protecting groups using trifluoroacetic acid and anisole. The starting material was prepared as follows:

A solution of phosphorus pentachloride (5.20 g) in dry dichloromethane (60 ml) at −10° was treated with N,N-dimethylacetamide (12 ml), and then with 2-(2-t-butoxycarbonylprop-2-yloxyimino)-2-(fur-2-yl)acetic acid (syn isomer) (6.43 g) added portionwise. The solution was stirred at −10° for 15 minutes and then ice (14 g) was slowly added and the temperature allowed to rise to 0° over 10 minutes. The organic layer was separated and added dropwise to a suspension of diphenylmethyl (1S,6R,7R)-7-amino-3-bromomethylceph-3-em-4-carboxylate 1-oxide hydrobromide (10.62 g) in dichloto stirred petrol (b.p. 40°–60°) to give a gummy precipitate. The supernatant was decanted off and the gum chromatographed on a column of Kieselgel, which was eluted with dichloromethane containing from 0 to 10% acetone. Eluant fractions containing the main product were combined and evaporated to a foam. Trituration with cyclohexane gave diphenylmethyl (1S,6R,7R)-3-bromomethyl-7-[2-(2-t-butoxycarbonylprop-2-yloxyimino)-2-(fur-2-yl)acetamido]ceph-3-em-4-carboxylate 1-oxide (syn isomer) as a pale yellow microcrystalline powder (13.61 g, 90%); $[\alpha]_D$ −22° (c 1.0, DMSO); $\lambda_{max}$ (EtOH) 281 nm ($\epsilon$ 22,200); $\nu_{max}$ (CHBr$_3$) 1800 cm$^{-1}$ (β-lactam); τ (d$_6$ DMSO) values include 1.26 (d, J 8 Hz, NH), 3.86 (dd, J 4 and 8 Hz; 7-H), 8.51 (s, C(CH$_3$)$_2$) and 8.61 (s, C(CH$_3$)$_3$).

TABLE 4

| Ex. No. | $R^q$ | P | Salt | $[\alpha]_D$ (DMSO) | $\gamma_{max}$,nm (pH 6 buffer) | $\epsilon$ | β-lactam $\nu_{max}$,cm$^{-1}$ (Nujol) | τ values* for d$_6$-DMSO at 100 MHz | | |
|---|---|---|---|---|---|---|---|---|---|---|
| | | | | | | | | x | y | $R^q$ |
| 8 | >C(CH$_3$)$_2$ | CH$_2$S-(pyridinium-N-CH$_3^+$) | trifluoroacetate | −14° | 277 | 21,500 | 1782 | 0.40 | 4.14 | 8.53 |

*Values for the trifluoroacetate salt

EXAMPLE A

This example illustrates the formulation of a pharmaceutical composition.

Dry Powder for Injection

Sterile (6R,7R)-7[2-carboxyprop-2-yloxyimino-2-(fur-2-yl)-acetamido]-3-(1-methyltetrazol-5-ylthiomethyl)-ceph-3-em-4-carboxylic acid, sodium salt (syn-isomer) is filled into glass vials, the claimed contents of each container being 500 mg. or 1.00g of the antibiotic, as desired. Filling is carried out asceptically under a blanket of nitrogen. The vials are closed using rubber discs or plugs held in position by aluminium sealing rings, thereby preventing gaseous exchange or ingress of micro-organisms. The product would be intended for reconstitution with water for injections or other suitable sterile vehicle shortly before administration.

We claim:

1. A compound selected from the group consisting of a cephalosporin antibiotic of the formula:

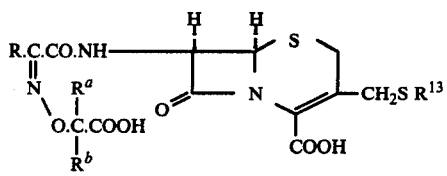

wherein
R is thienyl or furyl;
$R^a$ is hydrogen, methyl, ethyl, propyl, isopropyl, butyl, allyl, cyclohexyl or phenyl;
$R^b$ is hydrogen, carboxy, $C_2$-$C_5$ alkoxycarbonyl, methyl, ethyl, propyl, isopropyl, butyl, allyl, cyclohexyl or phenyl; or
$R^a$ and $R^b$ together with the carbon atom to which they are attached form a $C_{3-7}$ cycloalkylidene group; and
$R^{13}$ is $C_1$-$C_6$ alkyl, $C_3$-$C_7$ cycloalkyl, phenyl $C_1$-$C_6$ alkyl, phenyl, naphthyl, thiadiazolyl, diazolyl, triazolyl, tetrazolyl, thiazolyl, thiatriazolyl, oxazolyl, oxadiazolyl, pyridyl, pyrimidyl, benzimidazolyl, benzoxazolyl, benzothiazolyl, triazolopyridyl or purinyl;

and a physiologically acceptable salt, ester, or 1-oxide thereof.

2. The compound of claim 1 which is (6R,7R)-7-[2-carboxymethoxyimino-2-(fur-2-yl) acetamido]-3-(1-methyltetrazol-5-ylthiomethyl)ceph-3-em-4-carboxylic acid (syn isomer).

3. The compound of claim 1 which is (6R,7R)-7-[2-(2-carboxyprop-2-yloxyimino)-2-(fur-2-yl)acetamido]-3-(1-methyltetrazol-5-ylthiomethyl)ceph-3-em-4-carboxylic acid (syn isomer).

4. The compound of claim 1 which is (6R,7R)-7-[2-(1-carboxycyclopent-1-yloxyimino)-2-(fur-2-yl) acetamido]-3-(1-methyltetrazol-5-ylthiomethyl)ceph-3-em-4-carboxylic acid (syn isomer).

5. The compound of claim 1 which is (6R,7R)-7-[2-carboxymethoxyimino-2-(fur-2-yl)acetamido]-3-(triazol-4-ylthiomethyl)ceph-3-em-4-carboxylic acid (syn isomer).

6. The compound of claim 1 which is (6R,7R)-7-[2-(1-carboxycyclo-but-1-yloxyimino)-2-(fur-2-yl)acetamido]-3-(1-methyltetrazol-5-ylthiomethyl)-ceph-3-em-4-carboxylic acid (syn isomer).

7. The compound of claim 1 which is (6R,7R)-7-[2-carboxyprop-2-yloxyimino)-2-(fur-2-yl)acetamido]-3-(5-methyl-1,3,4-thiadiazol-2-ylthiomethyl)ceph-3-em-4-carboxylic acid (syn isomer).

8. A compound selected from the group consisting of a cephalosporin antibiotic of the formula:

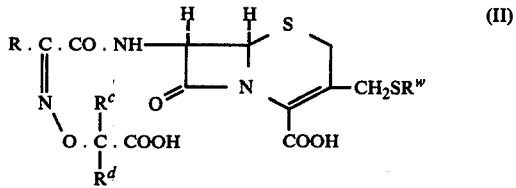

wherein R is thienyl or furyl, $R^c$ is methyl, ethyl, propyl, allyl or phenyl and $R^d$ is hydrogen, carboxy, methyl, ethyl, propyl, allyl or phenyl; or $R^c$ and $R^d$ together with the carbon atom to which they are attached form a cyclobutylidene, cyclopentylidene or cyclohexylidene group; and $R^w$ is selected from pyridyl, diazolyl, triazolyl, tetrazolyl, thiazolyl, thiadiazolyl, oxadiazolyl, or such a group substituted by a lower alkyl or phenyl; and a physiologically acceptable salt or 1-oxide thereof.

* * * * *